US006752149B2

(12) United States Patent
Gillespie et al.

(10) Patent No.: US 6,752,149 B2
(45) Date of Patent: Jun. 22, 2004

(54) NASAL MASK WITH REPLACEABLE FILTER

(75) Inventors: Michael R. Gillespie, Houston, TX (US); John B. Williamson, Houston, TX (US)

(73) Assignee: Realaid, Inc., Houston, TX (US)

( * ) Notice: Subject to any disclaimer, the term of this patent is extended or adjusted under 35 U.S.C. 154(b) by 0 days.

(21) Appl. No.: 10/202,959

(22) Filed: Jul. 25, 2002

(65) Prior Publication Data

US 2004/0020489 A1 Feb. 5, 2004

(51) Int. Cl.$^{7}$ .................... A61M 15/08

(52) U.S. Cl. .................... 128/204.12; 128/206.18; 128/207.13

(58) Field of Search .................... 128/204.12, 204.13, 128/206.11, 206.18, 207.13, 206.13

(56) References Cited

U.S. PATENT DOCUMENTS

| | | | | | |
|---|---|---|---|---|---|
| 369,019 | A | * | 8/1887 | McMaster | 128/204.12 |
| 390,027 | A | * | 9/1888 | Locke | 128/206.11 |
| 609,923 | A | * | 8/1898 | Tuttle | 128/203.29 |
| 628,111 | A | * | 7/1899 | McHatton | 128/206.18 |
| 630,242 | A | | 8/1899 | Lakin | |
| 701,538 | A | * | 6/1902 | Carence | 128/204.12 |
| 758,030 | A | * | 4/1904 | Carence | 128/204.12 |
| 790,057 | A | * | 5/1905 | Hively | 128/203.29 |
| ,958,569 | A | | 5/1910 | Venner | |
| 1,097,538 | A | * | 5/1914 | Cordova | 2/427 |
| 1,218,906 | A | * | 3/1917 | Shepherd | 128/204.12 |
| 1,297,337 | A | * | 3/1919 | Feltner | 128/206.13 |
| 1,359,073 | A | * | 11/1920 | King | 128/206.15 |
| 1,802,275 | A | * | 4/1931 | Roche | 128/206.11 |
| 1,914,418 | A | * | 6/1933 | Goyena | 128/206.18 |
| 2,056,692 | A | * | 10/1936 | Roche | 128/206.13 |
| 2,087,042 | A | * | 7/1937 | Phillips | 128/206.18 |
| 2,097,846 | A | | 11/1937 | Strauch | |
| 2,161,607 | A | * | 6/1939 | Anderson | 128/206.18 |
| 2,295,321 | A | * | 9/1942 | Anderson | 128/206.18 |
| 2,410,903 | A | * | 11/1946 | Rogge | 128/203.27 |
| 2,494,406 | A | | 1/1950 | Reitano | |
| 2,535,155 | A | * | 12/1950 | Pandorf | 128/204.12 |
| 2,572,254 | A | * | 10/1951 | Folberth | 128/206.18 |
| 2,890,695 | A | | 6/1959 | Safstrem | |
| 3,216,415 | A | | 11/1965 | Littleton | |
| 3,463,149 | A | | 8/1969 | Albu | |
| 3,603,315 | A | | 9/1971 | Becker | |
| 3,664,335 | A | | 5/1972 | Boucher et al. | |
| 3,699,958 | A | | 10/1972 | Szucs | |
| 3,747,597 | A | | 7/1973 | Olivera | |
| 3,774,601 | A | * | 11/1973 | Langone | 128/205.29 |
| 3,802,426 | A | | 4/1974 | Sakamoto | |
| 3,884,223 | A | | 5/1975 | Keindl | |
| 3,905,335 | A | | 9/1975 | Kapp | |
| 4,004,584 | A | * | 1/1977 | Geaney | 128/206.14 |
| 4,030,491 | A | | 6/1977 | Mattila | |
| 4,052,983 | A | | 10/1977 | Bovender | |
| 4,220,150 | A | | 9/1980 | King | |
| 4,240,420 | A | | 12/1980 | Riaboy | |
| 4,354,489 | A | | 10/1982 | Riaboy | |
| 4,984,302 | A | * | 1/1991 | Lincoln | 2/206 |
| D326,541 | S | | 5/1992 | McBrearty, Jr. | |
| 5,267,557 | A | * | 12/1993 | Her-Mou | 128/206.21 |
| 5,392,773 | A | * | 2/1995 | Bertrand | 128/206.11 |
| 5,485,836 | A | * | 1/1996 | Lincoln | 128/206.11 |
| 5,636,629 | A | * | 6/1997 | Patterson, Jr. | 128/207.13 |
| D383,537 | S | | 9/1997 | Lunden | |
| 6,098,624 | A | * | 8/2000 | Utamaru | 128/206.18 |
| D431,077 | S | | 9/2000 | McGinnis et al. | |
| 6,357,440 | B1 | | 3/2002 | Hansen et al. | |
| 6,584,975 | B1 | * | 7/2003 | Taylor | 128/206.11 |

FOREIGN PATENT DOCUMENTS

| | | |
|---|---|---|
| FR | 945897 | 5/1949 |
| FR | 1354867 | 2/1964 |

* cited by examiner

*Primary Examiner*—Aaron J. Lewis
(74) *Attorney, Agent, or Firm*—Mark A. Oathout

(57) ABSTRACT

A breathing filter with a nose mask, strap(s), and a filter member. The strap(s) are elastic, and serve to hold the nose mask over the user's nose. The filter member is a plug-in device allowing removal of the filter member and replacement of the filter member cartridge or the filter material.

20 Claims, 3 Drawing Sheets

NASAL MASK WITH REPLACEABLE FILTER

BACKGROUND

Individuals who are outside or exposed to various work environments can encounter a variety of air borne irritants. For example, walkers and joggers can be exposed to pollution, pollen, exhaust, insects, dust, smoke, bacteria, viruses, etc. There are also numerous other examples of individuals who are exposed to air irritants such as people who work in the sanitization industry, insect infested environments, dusty or sandy environments, painters, a chemical industry, construction workers, bike riders, skiers, fertilizing, crop dusting, exterminating and the list goes on. Animals and birds suffer as well from air borne irritants such as sand and dust including the other irritants and problems mentioned above which can lead to ailments such as lung disease. Moreover, negative effects are enhanced on individuals, animals and birds with respiratory conditions such as allergies and lung problems.

A variety of breathing filter devices have been available in the past, however, these devices have a variety of shortcomings, including devices which are too expensive to dispose of after one use or are not readily washable once they are covered with an irritant such as pollen, dust, mucus, devices which inhibit breathing, devices which are cost prohibitive, those which may not be sturdy specially in a moist environment, devices which are cumbersome to wear, the device may be unsightly to wear, etc.

The need therefore exists for a disposable breathing filter which is easy to apply, comfortable to wear, easy to remove, manufactured with inexpensive materials by an inexpensive process, disposable, washable, durable (especially for moist environments), lightweight and breathable.

SUMMARY

The breathing filter generally has a nose mask, strap(s), and a filter member. The strap(s) may be elastic, and serve to hold the nose mask over the user's nose. The filter member may be a plug-in device allowing removal of the filter member and replacement of the filter member cartridge or the filter material.

Certain embodiments of this invention are not limited to any particular individual features disclosed, but include combinations of features distinguished from the prior art in their structures and functions. Features of the invention have been described so that the detailed descriptions that follow may be better understood, and in order that the contributions of this invention to the arts may be better appreciated. These may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. This invention is to be read to include any legally equivalent devices or methods which do not depart from the spirit and scope of the present invention.

The present invention recognizes, addresses and meets its preferences or objectives in its various possible embodiments and equivalents thereof. To one of skill in this art that has the benefit of this invention's realizations, teachings, disclosures, and suggestions, other purposes and advantages will be appreciated from the following description and the accompanying drawings. The detail in the description is not intended to thwart this patent's object to claim this invention no matter how others may later disguise it by variations in form or additions of further improvements. These descriptions illustrate certain preferred embodiments and are not to be used to improperly limit the scope of the invention, which may have other equally effective or legally equivalent embodiments.

DETAILED DESCRIPTION

Figure 1:
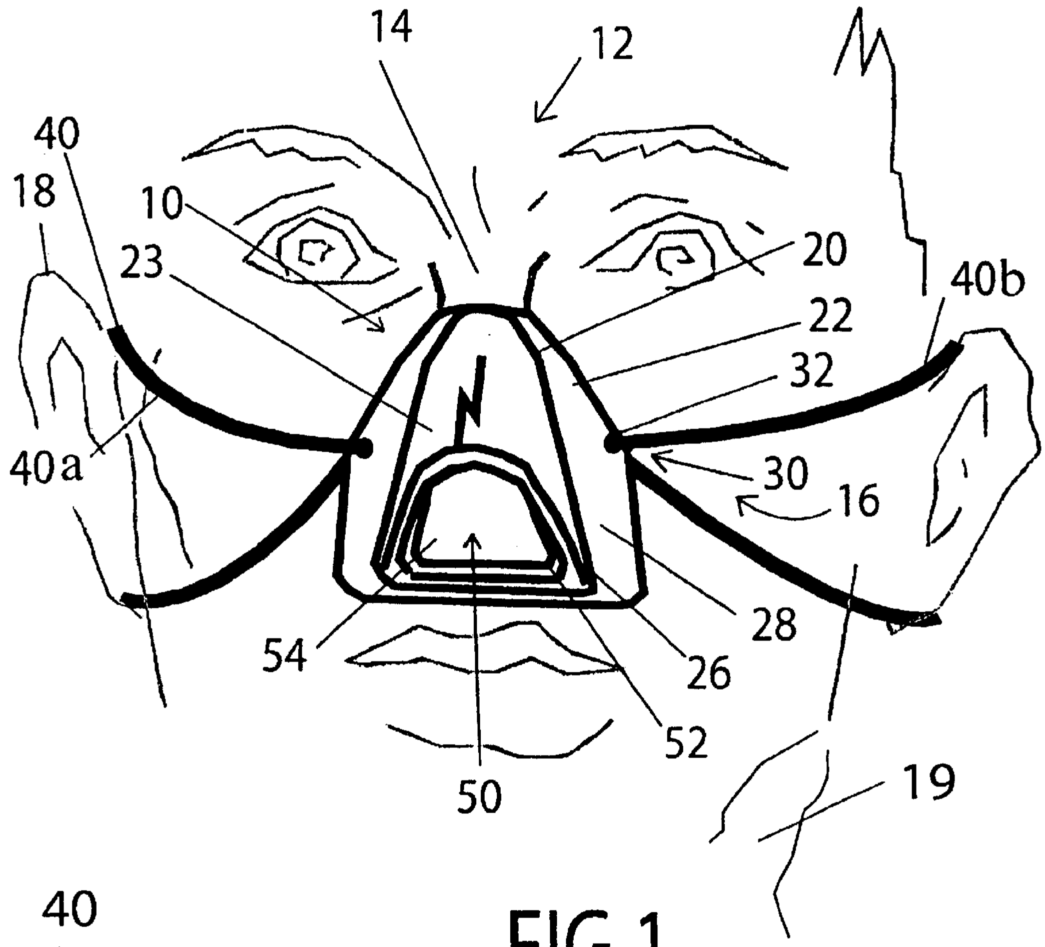
FIG. 1 is a front elevational view of an individual user wearing the nasal mask and air filter.
Figure 3:
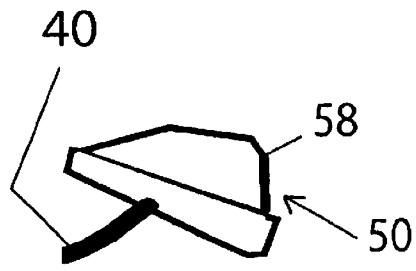
FIG. 3 shows a side view of the nasal mask and air filter.
Figure 2:
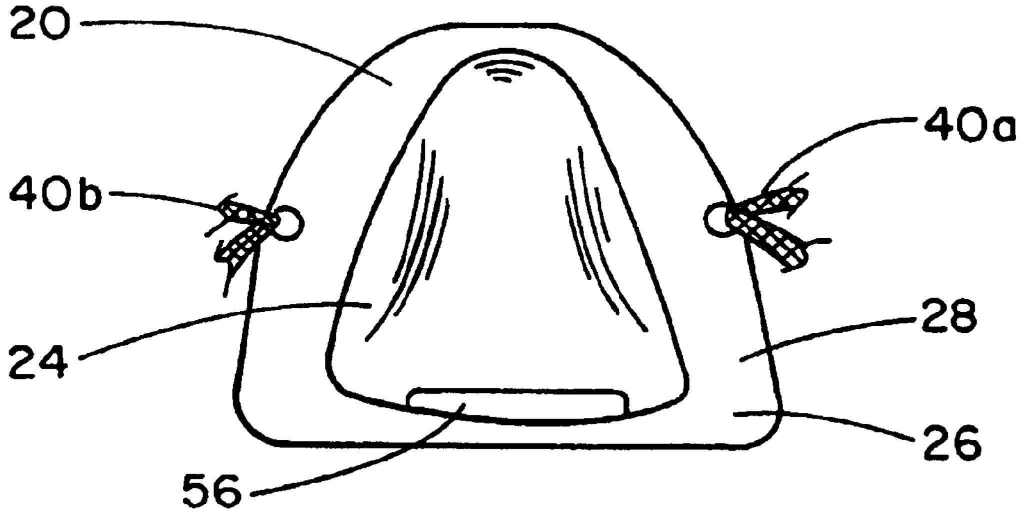
FIG. 2 shows a backside view of the nasal mask and air filter.
Figure 4:
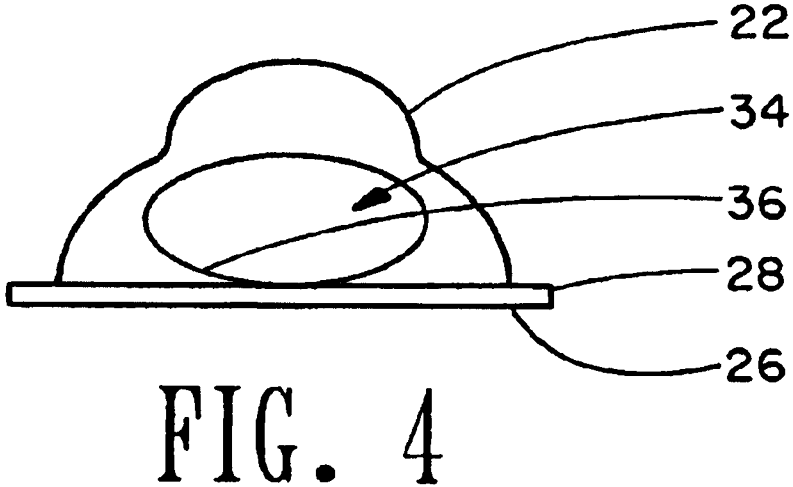
FIG. 4 shows a bottom view of the nasal mask with the filter member removed.
Figure 5:
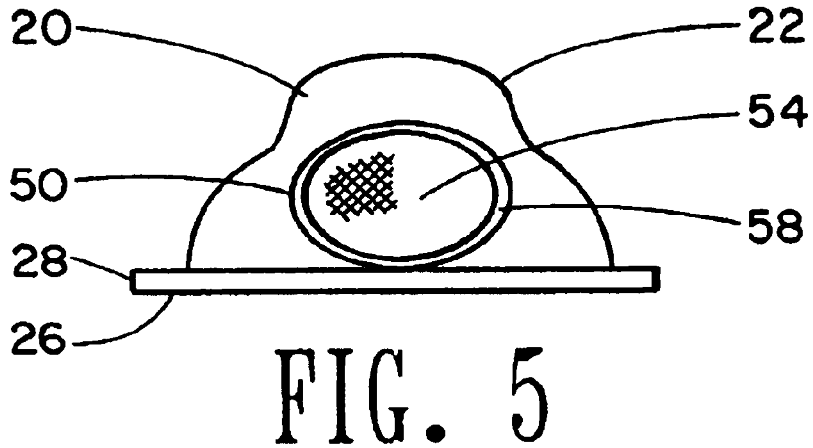
FIG. 5 shows a bottom view of the nasal mask with the filter member inserted.
Figure 6:
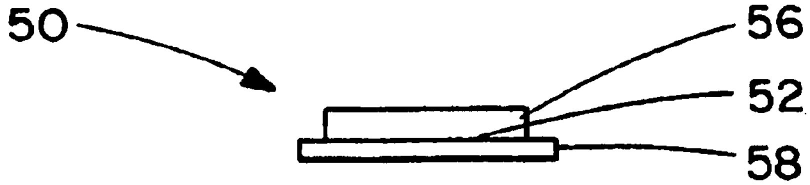
FIG. 6 shows an elevational view of the filter member.
Figure 7:
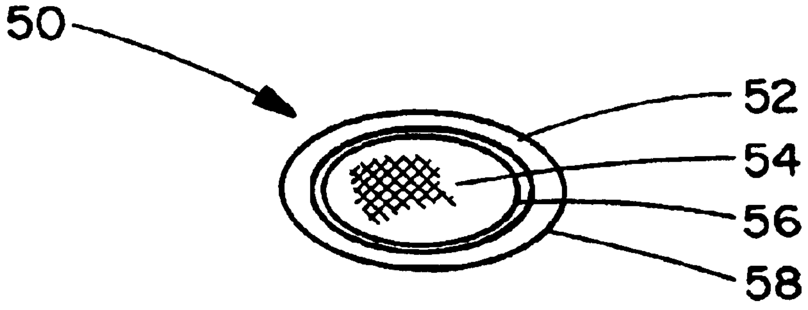
FIG. 7 shows a top view of the filter member.

Referring to FIGS. 1–7, the nasal mask and filter 10 generally has a nose mask 20, strap(s) 40, and a filter member 50. The strap(s) 40*a* & *b* may be elastic, and hold the nose mask 20 over the user's 12 nose 14. The filter member 50 may be in the form of a plug-in device for removing the filter member 50 and plugging a replacement filter member 50 (i.e. a replaceable cartridge) back into the nose mask 20, or for removing the filter member 50, replacing the filter material 54 and plugging the filter member 50 back into the nose mask 20.

The nose mask 20 may be a molded member 22. It has a concave inner surface 24 contoured to fit over the nose 14 of the user 12. The nose mask 20 also has a terminating surface 26 which seals against the face 16 of the user 12 when the nose mask 20 is worn. The terminating surface 26 may be molded with and become unitary with the molded member 22, or it may be a separate mounting base 28. The terminating surface 26, which as shown in the drawings is the mounting base 28 attached around an entire periphery of the nose mask 20, and has holes 30 which may be reinforced by eyelets 32. The mounting base 28 may be made of a soft, pliable material, such as, for example, a foam, for cushion, comfort and for sealing against the face 16 of the user 12.

The molded member 22 may be shaped to have an outer surface 23 in conformity with the contours/appearance of a human nose (and may even be made to resemble any particular desirable nose). The molded member 22 may be made of a semi-rigid or of a rigid material. It may also be made in any color and/or texture, such as, for example, a texture and/or color to mimic the appearance of human skin.

The lower end of the nose mask 20 is adapted for the connection of a filtration unit/filter member 50. More specifically, a portion (near the lower end) of the nose mask 20 has an opening 34 which is proximate the user's nostrils (not shown) when the nose mask 20 is worn by the user 12.

The filter member 50 has a support frame 52 and a filtration material 54. The support frame 52 is annular with a generally curved shape (although other shapes could be used) and defines a central opening. The shape and size should however be made within the confines of the shape and size of the lower end of the nose mask 20. The filtration material 54 may be made of any suitable filter material and may be inserted into the opening or placed over the opening allowing the user 12 to breath through the filtration material 54. The support frame 52 supports the filtration material 54.

The support frame 52 of the filter member 50 has outer sidewalls 56 adapted to be biased/wedged into (like a leaf spring) the sidewalls 36 defining the opening 34 to the nose mask 20, or the filter member 50 could "snap-in" to the nose mask 20 via the sidewalls 56 and the sidewalls 36 being made with any known "snap-in" structure (i.e. slot and rim). The lower end of the support frame 52 has a protuberant rim 58 which seats against the nose mask 20 around the opening. This prevents the user from inserting the filter member 50 too far into the nose mask 20. Hence, the filter member 50 is essentially adapted to be plugged into the nose mask 20. Accordingly, the filter member 50 is mounted to (or snapped/plugged into) the sidewalls 36 of the nose mask 20.

The strap(s)/headband(s) 40 may be laces or elastic, and one or more straps (40*a* and 40*b* are shown) may be used to attach the nasal mask and filter 10 around the face/head 16, ears 18 or neck 19. The straps 40*a* and 40*b* shown are elastic loops which are connected to the terminating surface 26 around the eyelets 32. The straps 40*a* and 40*b* hold the nose mask 20 over the user's nose 14 by wrapping one of each respective straps 40*a* and 40*b* behind the ears 18 of the user 12. Thereafter, the user 12 may begin to breath through the filter member 50. Periodically, the filter member 50 may be removed for replacement of the filter member 50 or for replacement of the filter material 54. After replacement the filter member 50 may be plugged back into the nose mask 20.

Medicated or non-medicated substance(s) may be added to the filter member 50 to benefit or promote the health of the user 12 or to kill germs which could be breathed out of the user's nostrils. Hence, medical delivery substances, such as, for example, a nose drop type medication could be added as a decongestant or antihistamine, or lavender could be added for insomnia for therapeutics/benefiting the health of the user 12 or others.

In conclusion, therefore, it is seen that the present invention and the embodiment(s) disclosed herein are well adapted to carry out the objectives and obtain the ends set forth. Certain changes can be made in the subject matter without departing from the spirit and the scope of this invention. It is realized that changes are possible within the scope of this invention and it is further intended that each element or step recited is to be understood as referring to all equivalent elements or steps. The description is intended to cover the invention as broadly as legally possible in whatever forms it may be utilized.

What is claimed is:

1. A breathing filter for wearing over a user's nose and surrounding the user's nostrils, comprising:

a nose mask including a concave inner surface contoured to fit over the user's nose and terminating in a surface sealing against a user's face when said nose mask is worn by the user, and having an opening which is located proximate the user's nostrils when said nose mask is worn by the user;

wherein said surface sealing against the user's face comprises a mounting base made of a soft, pliable material attached around an entire periphery of said nose mask on a side of said nose mask located proximate the user's face when said nose mask is worn by the user;

a strap connected to said nose mask for holding said nose mask over the user's nose; and a filter member wherein said filter member is adapted for mounting to the opening of said nose mask.

2. The apparatus according to claim 1, wherein said filter member includes a support frame and a filtration material mounted to the support frame.

3. The apparatus according to claim 2, wherein the support frame comprises a semi-annular member having a protuberant rim located on a lower end, wherein said semi-annular member has a means for biasing against said nose mask when said filter member is mounted to the opening of said nose mask.

4. The apparatus according to claim 3, wherein said means for biasing comprises a means for wedging into the opening of said nose mask, said means for wedging being located above the protuberant rim.

5. The apparatus according to claim 1 wherein said nose mask includes an outer surface having a means for appearing and resembling an entire desirable human nose.

6. The apparatus according to claim 1 wherein said nose mask is made of a semi-rigid material.

7. The apparatus according to claim 1 wherein said nose mask is made of a rigid material.

8. The apparatus according to claim 1 wherein said filter member is a replaceable cartridge.

9. The apparatus according to claim 1, wherein said mounting base has eyelets for attaching the strap to said mounting base.

10. The apparatus according to claim 1, wherein the strap comprises an elastic strap.

11. The apparatus according to claim 1, wherein the strap comprises two elastic loops adapted to fit around the user's ears.

12. A breathing filter for wearing over a user's nose and surrounding the user's nostrils, comprising:

a nose mask including a concave inner surface contoured to fit over the user's nose and terminating in a surface sealing against a user's face when said nose mask is worn by the user, and having an opening which is located proximate the user's nostrils when said nose mask is worn by the user;

a strap connected to said nose mask for holding said nose mask over the user's nose;

a filter member wherein said filter member is adapted for mounting to the opening of said nose mask; and further including a medical delivery substance added to said filter member.

13. The apparatus according to claim 12, wherein said filter member includes a support frame and a filtration material mounted to the support frame; and wherein the support frame comprises a semi-annular member having a protuberant rim located on a lower end, wherein said semi-annular member has a means for biasing against said nose mask when said filter member is mounted to the opening of said nose mask.

14. A breathing filter for wearing over a user's nose and surrounding the user's nostrils, comprising:

a nose mask including a concave inner surface contoured to fit over the user's nose and terminating in a surface sealing against a user's face when said nose mask is worn by the users, and having an opening which is located proximate the user's nostrils when said nose mask is worn by the user;

a strap connected to said nose mask for holding said nose mask over the user's nose;

filter member wherein said filter member is adapted for mounting to the opening of said nose mask;

wherein said filter member includes a support frame and a filtration material mounted to the support frame; and wherein the support frame comprises a semi-annular member having a protuberant rim located on a lower end, wherein said semi-annular member has a means for biasing against said nose mask when said filter member is mounted to the opening of said nose mask.

15. The apparatus according to claim 16, wherein said surface sealing against the user's face comprises a mounting base made of a soft, pliable material attached to said nose mask on a side of said nose mask located proximate the user's face when said nose mask is worn by the user.

16. The apparatus according to claim 14 further including a medical delivery substance added to said filter member.

17. The apparatus according to claim 14 wherein said nose mask includes an outer surface in conformity with contours of a human nose.

18. The apparatus according to claim 14 wherein said nose mask is made of a semi-rigid material.

19. The apparatus according to claim 14, wherein the strap comprises two elastic loops adapted to fit around the user's ears.

20. The apparatus according to claim 14, wherein said means for biasing comprises a means for wedging into the opening of said nose mask, said means for wedging being located above the protuberant rim.

* * * * *